(12) United States Patent
Kunze et al.

(10) Patent No.: US 9,320,488 B2
(45) Date of Patent: Apr. 26, 2016

(54) METHOD AND DEVICE FOR CORRECTION OF MOVEMENT ARTIFACTS IN A COMPUTED TOMOGRAPHY IMAGE

(71) Applicants: Holger Kunze, Bubenreuth (DE); Yiannis Kyriakou, Spardorf (DE)

(72) Inventors: Holger Kunze, Bubenreuth (DE); Yiannis Kyriakou, Spardorf (DE)

(73) Assignee: Siemens Aktiengesellschaft, München (DE)

( * ) Notice: Subject to any disclaimer, the term of this patent is extended or adjusted under 35 U.S.C. 154(b) by 33 days.

(21) Appl. No.: 14/179,301

(22) Filed: Feb. 12, 2014

(65) Prior Publication Data
US 2014/0226891 A1    Aug. 14, 2014

(30) Foreign Application Priority Data
Feb. 13, 2013  (DE) .......................... 10 2013 202 313

(51) Int. Cl.
| | |
|---|---|
| G06K 9/00 | (2006.01) |
| A61B 6/00 | (2006.01) |
| G06T 11/00 | (2006.01) |
| A61B 6/03 | (2006.01) |

(52) U.S. Cl.
CPC .............. *A61B 6/5264* (2013.01); *A61B 6/032* (2013.01); *G06T 11/008* (2013.01); *G06T 2211/412* (2013.01)

(58) Field of Classification Search
None
See application file for complete search history.

(56) References Cited

U.S. PATENT DOCUMENTS

| | | | |
|---|---|---|---|
| 4,144,569 A * | 3/1979 | Wagner ........................... 378/11 |
| 5,579,358 A | 11/1996 | Lin | |
| 6,243,439 B1 | 6/2001 | Arai et al. | |
| 6,256,364 B1 * | 7/2001 | Toth et al. ......................... 378/4 |
| 6,944,260 B2 * | 9/2005 | Hsieh et al. ...................... 378/19 |
| 7,187,745 B2 * | 3/2007 | Flohr et al. ........................ 378/8 |
| 7,583,830 B2 * | 9/2009 | Schreiber et al. ............. 382/131 |
| 7,630,528 B2 * | 12/2009 | Kohler et al. ................. 382/128 |
| 7,929,659 B2 * | 4/2011 | Wu et al. ........................... 378/4 |
| 2004/0097805 A1 * | 5/2004 | Verard et al. ................... 600/428 |
| 2004/0114727 A1 * | 6/2004 | Yan et al. ....................... 378/210 |
| 2004/0120450 A1 * | 6/2004 | Flohr et al. ........................ 378/4 |
| 2005/0100124 A1 * | 5/2005 | Hsieh et al. ....................... 378/4 |

(Continued)

FOREIGN PATENT DOCUMENTS

DE    102008008611 A1    9/2009

OTHER PUBLICATIONS

Wicklein et al. "An online motion- and misalignment-correction method for medical flat-detector CT", Proc. SPIE 8668, Medical Imaging 2013: Physics of Medical Imaging, 86681S (Mar. 6, 2013).*

(Continued)

*Primary Examiner* — Aaron W Carter
(74) *Attorney, Agent, or Firm* — Lempia Summerfield Katz LLC

(57) ABSTRACT

A method for correction of movement artifacts in a computed tomography image that is reconstructed from a plurality of computed tomography projection images is provided. Using all projection images of the plurality of computed tomography projection images, an average position of an examination area of an examination object in the reconstructed image volume is determined by a global optimization method. With the aid of the at least one image volume block that is formed from predeterminable projection images, the movement of the examination area of the examination object in the at least one image volume block is estimated by an optimization method. A corresponding device for correction of movement artifacts in a computed tomography image is also provided.

15 Claims, 4 Drawing Sheets

(56) References Cited

U.S. PATENT DOCUMENTS

| | | | |
|---|---|---|---|
| 2005/0148850 A1* | 7/2005 | Lahm et al. | 600/407 |
| 2005/0249431 A1* | 11/2005 | Ruhmschopf | 382/274 |
| 2007/0103464 A1* | 5/2007 | Kaufman et al. | 345/424 |
| 2008/0044076 A1* | 2/2008 | Spies | 382/132 |
| 2008/0253635 A1* | 10/2008 | Spies et al. | 382/131 |
| 2008/0273651 A1* | 11/2008 | Boas | 378/4 |
| 2009/0147916 A1* | 6/2009 | Fallone et al. | 378/65 |
| 2009/0149741 A1* | 6/2009 | Heigl | 600/424 |
| 2009/0202034 A1 | 8/2009 | Lauritsch et al. | |
| 2010/0020921 A1* | 1/2010 | Dong et al. | 378/19 |
| 2011/0103542 A1* | 5/2011 | Allmendinger et al. | 378/4 |
| 2011/0116697 A1* | 5/2011 | Dafni et al. | 382/131 |
| 2011/0142313 A1* | 6/2011 | Pack et al. | 382/131 |
| 2011/0286573 A1* | 11/2011 | Schretter et al. | 378/4 |
| 2012/0207370 A1* | 8/2012 | Fahimian et al. | 382/131 |
| 2012/0250820 A1* | 10/2012 | Haras et al. | 378/9 |
| 2013/0028536 A1* | 1/2013 | Hazard | 382/275 |
| 2013/0177213 A1* | 7/2013 | Lee et al. | 382/107 |
| 2013/0259344 A1* | 10/2013 | Petersilka et al. | 382/131 |
| 2013/0303898 A1* | 11/2013 | Kinahan et al. | 600/425 |
| 2014/0226891 A1* | 8/2014 | Kunze et al. | 382/131 |
| 2014/0270450 A1* | 9/2014 | Grass et al. | 382/131 |
| 2014/0307935 A1* | 10/2014 | Ishii et al. | 382/131 |
| 2015/0201910 A1* | 7/2015 | Zhao et al. | 600/424 |

OTHER PUBLICATIONS

Y. Kyriakou, et al., "Simultaneous misalignment correction for approximate circular cone-beam computed tomography," Physics in Medicine and Biology, vol. 53, pp. 6267-6289, 2008.

J. Wicklein, et al., "Comparison of Image Features for Misalignment Correction in Flat-Detector CT," Second International Conference on Image Formation in X-Ray Computed Tomography, pp. 1-4, 2012.

J. Wicklein, et al., "An Object-Independent Measure for Improving Misalignment Correction in C-Arm CT," The 11$^{th}$ International Meeting on Fully Three-Dimensional Image Reconstruction in Radiology and Nuclear Medicine, pp. 145-148, 2011.

J. Wicklein, et al., "Image features for misalignment correction in medical flat-detector CT," Medical Physics, vol. 39, No. 8, pp. 4918-4931, 2012.

German Office Action for related German Application No. 10 2013 202 313.8, mailed Jul. 17, 2015, with English Translation.

* cited by examiner

METHOD AND DEVICE FOR CORRECTION OF MOVEMENT ARTIFACTS IN A COMPUTED TOMOGRAPHY IMAGE

This application claims the benefit of DE 10 2013 202 313.8, filed on Feb. 13, 2013, which is hereby incorporated by reference in its entirety.

BACKGROUND

The present embodiments relate to correction of movement artifacts in a computed tomography image.

With the aid of computed tomography (CT), sectional images or slice images may be created with the aid of a computer and suitable image processing algorithms from a plurality of x-ray images or x-ray recordings (e.g., projections or projection images) that are recorded from different directions and over an angular range of more than 180° around the object. The grayscales of the sectional images essentially reflect the x-ray absorption coefficients of the irradiated material. Other names for computed tomography are CT scan or CAT scan, from computed axial tomography. In general, the aim of CT or x-ray image recordings is to record an image of an area under examination (e.g., a lung of an object under examination such as a human or animal patient). In such cases, the assumption is made that the object to be reconstructed does not move during the recording.

For computed tomography of living patients, this assumption may be incorrect, since the patient moves or the device does not perform the calibrated movement exactly but deviates from the movement. The results of these movements are image errors (e.g., movement artifacts) that may show as unsharp image areas or shadow images. For the correction or reduction of movement artifacts, movement-correction methods that are based, for example, on markers or specific features and that estimate the movement have been developed. Such a method has been presented by J. Wicklein, H. Kunze, W. A. Kalender, Y. Kyriakou in "Comparison of Image Features for Misalignment Correction in Flat-Detector CT," Second International Conference on Image Formation in X-Ray Computed Tomography, Jun. 24-27, 2012, Fort Douglas/Olympic Village, Salt Lake City, Utah, USA.

In the feature-based methods, the movement of the object is estimated by minimization of a cost function. The entropy of the reconstructed object may be used as the cost function, for example.

From the literature (e.g., Y. Kyriakou, R. M. Lapp, L. Hillebrand, D. Ertel and W. A. Kalender, "Simultaneous misalignment correction for approximate circular cone-beam computed tomography," 2008, Phys. Med. Biol. 53, pp. 6267-6289), it is known that by a global optimization of the geometry parameters, in which, for example, the detector offset is determined in relation to the focus position for all projections together, an improvement of the reconstruction results may be achieved. The optimization is undertaken for this purpose with the aid of a simplex algorithm. The disadvantage of this method is that more complex movements may not be compensated for.

Other approaches determine the movement with the aid of a projection-based method, which is insensitive to small movements, such as are typically present in applications in the neurological area. This provides that the corresponding area of application is restricted to these or similar problem areas. These methods also rely on features that have a significant effect on the projections.

SUMMARY AND DESCRIPTION

The scope of the present invention is defined solely by the appended claims and is not affected to any degree by the statements within this summary. The present embodiments may obviate one or more of the drawbacks or limitations in the related art. For example, correction of movement artifacts in a computed tomography image that reduces the disadvantages of the described methods and also makes rapid processing of CT images possible is provided.

A method for correction of movement artifacts in a computed tomography image that is reconstructed from a plurality of computed tomography projection images is provided. Initially, using all projection images, an average position of an examination area of an examination object in the reconstructed image volume is determined by a global optimization method. With the aid of at least one image volume block that is formed from predeterminable projection images, the movement of the examination area of the examination object in the at least one image volume block is estimated by an optimization method.

Advantageously, the average position of the examination area of the examination object in the reconstructed image volume determined by the global optimization method is included in the selection of the predeterminable projection images of the at least one image volume block.

At least two image volume blocks are usefully formed from predeterminable projection images, and at least one projection image belongs to the at least two image volume blocks.

In one embodiment, the predeterminable projection images of an image volume block in each case are determined indirectly or directly by the result of an entry by a user.

With a direct entry, the projection images are predetermined directly (e.g., by specifying image numbers). An indirect entry uses a further intermediate act such as, for example, the assignment of a user entry to the image numbers using a table (e.g., a look-up table).

In one embodiment, the user entry is a speed of movement, and the predeterminable projection images of an image volume block in each case are consecutive projection images.

In one embodiment, the selection of predeterminable projection images of the at least one image volume block includes a measured breathing phase of the examination object and/or a measured heart phase of the examination object.

In one embodiment, the estimation of the movement of the examination area of the examination object in the at least one image volume block is executed repeatedly. With each repetition, the at least one image volume block is formed from fewer predeterminable projection images.

In a further advantageous embodiment, the repetitions are performed until such time as the at least one image volume block includes a single projection image.

A further advantageous embodiment makes provision for the entropy of the reconstructed computed tomography image to be included in the optimization process for determining the average position of the examination area of the examination object in the reconstructed image volume and/or where the entropy of the image volume block is included in the optimization method for estimating the movement of the examination area of the examination object in the at least one image volume block.

In one embodiment, at least one optimization method includes a gradient descent method.

In one embodiment, at least two image volume blocks may be taken into consideration for estimating the movement of the examination area of the examination object, and the at least two image volume blocks may overlap. The result of the estimation of the movement of the examination area of the examination object of an image volume block may be included in the estimation of the movement of the examination area of the examination object of the subsequent image volume block.

In one embodiment, the estimations of the movement of the examination area of the examination object of all image volume blocks are included in the correction of movement artifacts of the computed tomography image that is reconstructed from a plurality of computed tomography projection images.

In an advantageous development, the predeterminable projection images of an image volume block are dictated by the result of a user entry that defines a region and/or an organ.

In a further embodiment, a histogram analysis of the projection images is included in the selection of the predeterminable projection images of an image volume block.

In one embodiment, at least one method act may be executed automatically.

Automatically executed methods have the advantage of generally being executable more quickly, since fewer user entries are needed, and the error probability is mostly reduced.

Thus, a method is proposed in which the optimization of the cost function based on a reconstructed volume (e.g., the entropy) is performed in a number of acts with the aid of a gradient descent method.

Optimization is a subarea of applied mathematics that deals with finding optimum parameters of the system. A target function (e.g., a cost function) is minimized or maximized for an optimum parameter. Optimization methods are thus methods known from mathematics.

The gradient descent method (e.g., the steepest descent method) is a method that is used in mathematics to solve general optimization problems. In this method, the usual starting point is an approximation value, from which the direction of the negative gradient (e.g., that specifies the direction of the steepest descent from this approximation value) is followed until no further numerical improvement may be achieved. This value is interpreted as the optimum.

An embodiment provides for the following method of operation:

1. Global optimization: In this case, with the aid of all projection images (e.g., projections), an average position of the examination area (e.g., of an organ or of a vessel of an examination object such as a human patient) is specified. In one embodiment, an average position of the examination object is specified as a whole (e.g., the examination area is the same as the examination object).

2. Block-by-block optimization: Based on global optimization, the projection images are subsequently grouped into image volume blocks (e.g., blocks). For all projections together that belong to a block, the movement of the patient is estimated. Use is made of the fact that the movement in the projections of a block is similar. A projection may also belong to a number of blocks if a slow movement is involved. The blocks may also be refined from iteration to iteration until the projection type optimization is achieved. The refinement of blocks describes the reduction of the blocks by taking account of fewer projections.

3. Projection-by-projection optimization: After the block-by-block optimization, a projection-by-projection optimization of the movement estimation, which takes account of the fact that the movement for the individual projection does not correspond to the average movement in the block may be carried out.

Various criteria that may be utilized may be provided for the selection of the blocks: a) if a slow, non-periodic movement is assumed, the movement may be compared for consecutive projections. Thus, consecutive projections are assigned to one block. The block size may be adapted to the assumed speed of the movement. This may be done by a user entry, for example, in which a user (e.g., an MTA or a doctor) pre-specifies a movement speed. A block size may be calculated, even automatically, by the image recording frequency. In this case, the predeterminable projection images of an image volume block in each case are specified indirectly by the result of the user entry. A direct entry would be, for example, directly entering the projections (e.g., by specifying the image indices that are assigned to a block).

b) With periodic movements such as heartbeat or breathing, for example, the blocks may also be allocated based on these parameters. With heartbeat or breathing, all projections that have been recorded for the same heart phase or breathing phase are combined in a block.

A continuous movement may be estimated more easily through overlapping blocks that take account of the movement estimated in the previous block.

If the block size is increasingly refined, a hierarchical movement estimation that is suitable for uncoordinated patient movement is obtained.

A further problem of feature-based methods is the high computing outlay of these methods when applied to the entire volume of a CT image dataset. Often, however, only one area is responsible for the movement, or the movement may be detected well in one area because of the structures. Previously, this disadvantage was taken into account, or a part area to be optimized was selected experimentally or in a trial-and-error method (e.g., by repeated trial-and-error).

In order to reduce the calculation time of the algorithm, for the minimization of the cost function, only areas that are of significance for a later diagnosis and/or such areas that are well suited for estimating movement may be selected. This may be done, for example, by the automatic segmentation of the organ to be diagnosed (e.g., a liver segmentation). The segmentation is a subdiscipline of digital image processing and of machine vision. In technical literature, a plurality of methods for segmentation (e.g., for creating content-contiguous regions by combining adjacent picture elements (pixels) spatially by combining adjacent volume elements (voxels) in accordance with a specific homogeneity criterion) are known. Examples are pixel, edge and region-oriented methods. In addition, model-based methods, in which the starting point is a specific form of the objects, and also texture-based methods, in which an inner homogeneous structure of the objects may be taken into account are known. Advantageously, the information as to which organ or which region is of significance or of interest for a user may be obtained by selecting an organ program. Organ programs are known from clinical practice in imaging systems.

Areas with much structure (e.g., areas that show up as high-contrast in the x-ray images, such as bones or iodine-contrasted vessels) may be used for estimation of movements. The areas may be determined, for example, by evaluating the local standard deviation. Areas with much structure may have a higher standard deviation than homogeneous areas. A user may also restrict the areas of interest via a graphical user interface and thus contribute to the reduction of the computing time or to the improvement of the result.

In one embodiment, a device for correction of movement artifacts in computed tomography images includes a computed tomograph and a processing and control device. The processing and control device is configured to receive computed tomography projection images from the computed tomograph and reconstruct the computed tomography projection images into a computed tomography image. The processing and control device is configured to execute a method for correction of movement artifacts in a computed tomography image.

The processing and control device may be configured as a computer, for example, that is configured through a corresponding computer program to execute a previously described method. Advantageously, the processing and control device has an input device for the input of user entries (e.g., a keyboard) and has an output device (e.g., a computer monitor) for the output of results, such as a movement-compensated sectional image or slice image, for example.

DETAILED DESCRIPTION

DETAILED DESCRIPTION

Figure 1:
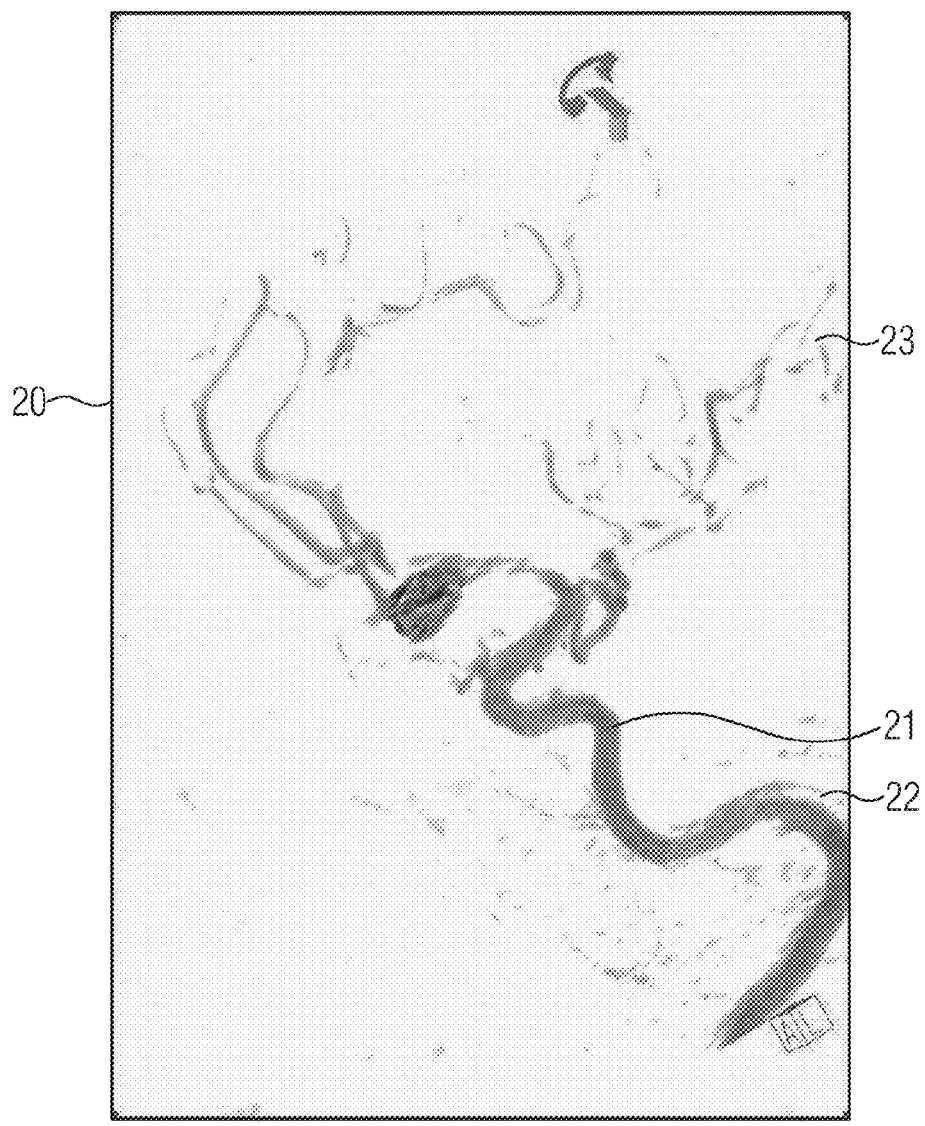
FIG. 1 shows an inverted slice image of a blood vessel in accordance with the prior art.

FIG. 1 shows an inverted slice image 20 of a blood vessel 21 in accordance with the prior art. The slice image 20 is a section through a spatial computed tomography image. The blood vessel 21 possesses a main stem 22 and branches 23. The slice image 20 is used for comparison with a slice image that has been processed by one embodiment of a method and is shown in FIG. 3.

Figure 2:
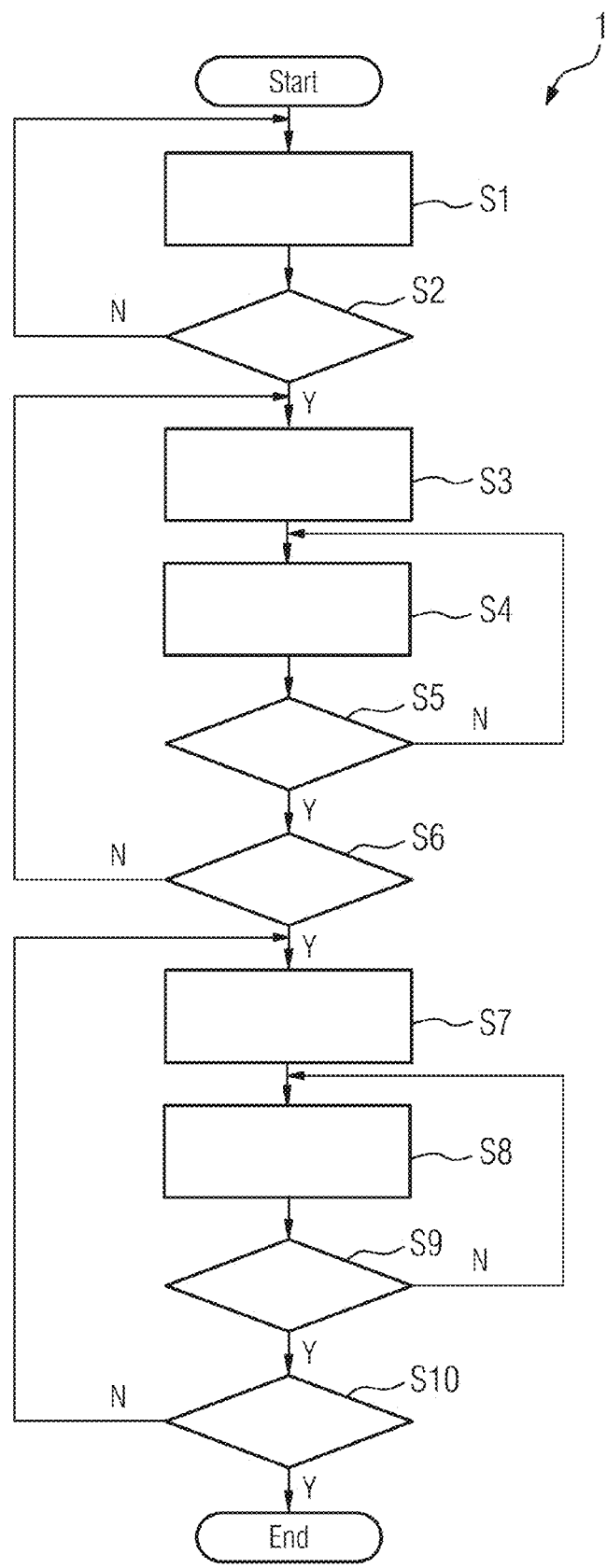
FIG. 2 shows an exemplary embodiment of a method for correction of movement artifacts in a computed tomography image.

FIG. 2 shows an example of a flow diagram of one embodiment of a method 1 for correction of movement artifacts in a computed tomography image. The method 1 includes acts S1 to S10. The method 1 begins, "Start", with method act S1 and ends, "End", after method act S10. In branches, "Y" provides that this branch is followed when the condition is fulfilled, corresponding to a response of "yes, the condition is fulfilled". "N" accordingly provides that this path is followed when the condition is not fulfilled (e.g., a response of "no, the condition is not fulfilled"). The individual method acts are as follows: S1) Execution of a "global optimization" act (e.g., calculation of a value of a target function with a current parameter); S2) interrogation: "change less than a specified limit?"; if "no", then change the parameter and continue with method act S1, else continue with method act S3; S3) first block selection; S4) execution of a "block-by-block optimization" act (e.g., calculation of a value of a target function with a current parameter); S5) interrogation: "change less than a specified limit?"; if "no", then change the parameter and continue with method act S4, else continue with method act S6; S6) Interrogation: "Is last block reached?"; if "no" then continue with method act S3 and select next block, else continue with method act S7; S7) second block selection; S8) execution of a "block-by-block optimization" act (e.g., calculation of a value of a target function with a current parameter); S9) interrogation: "Is last block reached?"; if "no" then continue with method act S8 and select next block, else continue with method act S10; S10) interrogation: "Is last block reached?"; if "no" then continue with method act S7 and select next block, else end "End" the method.

Figure 3:
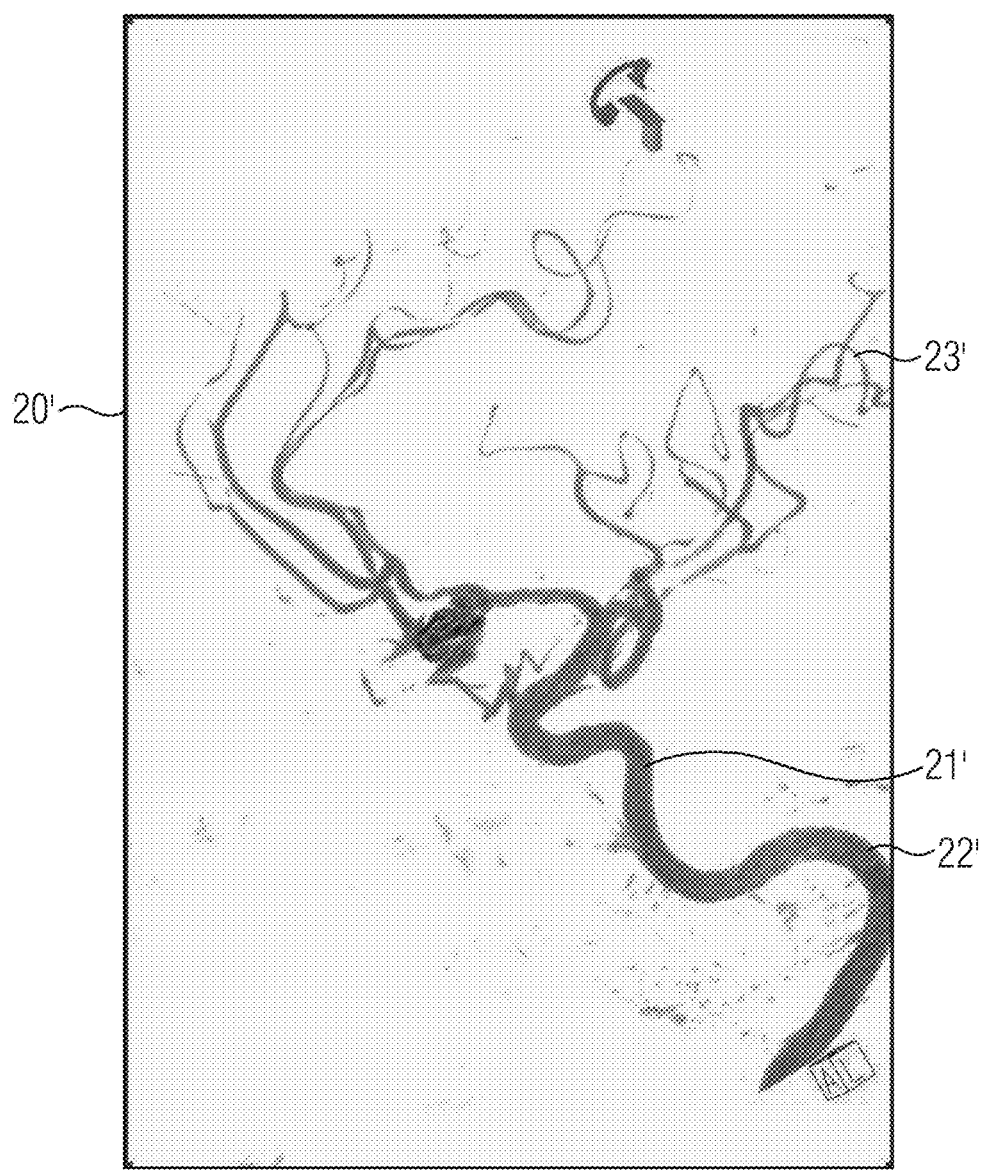
FIG. 3 shows an exemplary inverted slice image of a blood vessel after execution of one embodiment of a method.

FIG. 3 shows an exemplary inverted slice image 20' of a blood vessel 21' after execution of one embodiment of a method. The slice image 20' is a section through a spatial computed tomography image. The blood vessel 21' possesses a main stem 22' and branches 23'. By comparison with the slice image 20 from FIG. 1, the main stem 22' is shown far more clearly. In the area of the branches 23', a curve is able to be discerned, which is interrupted in FIG. 1 at reference character 23.

Figure 4:
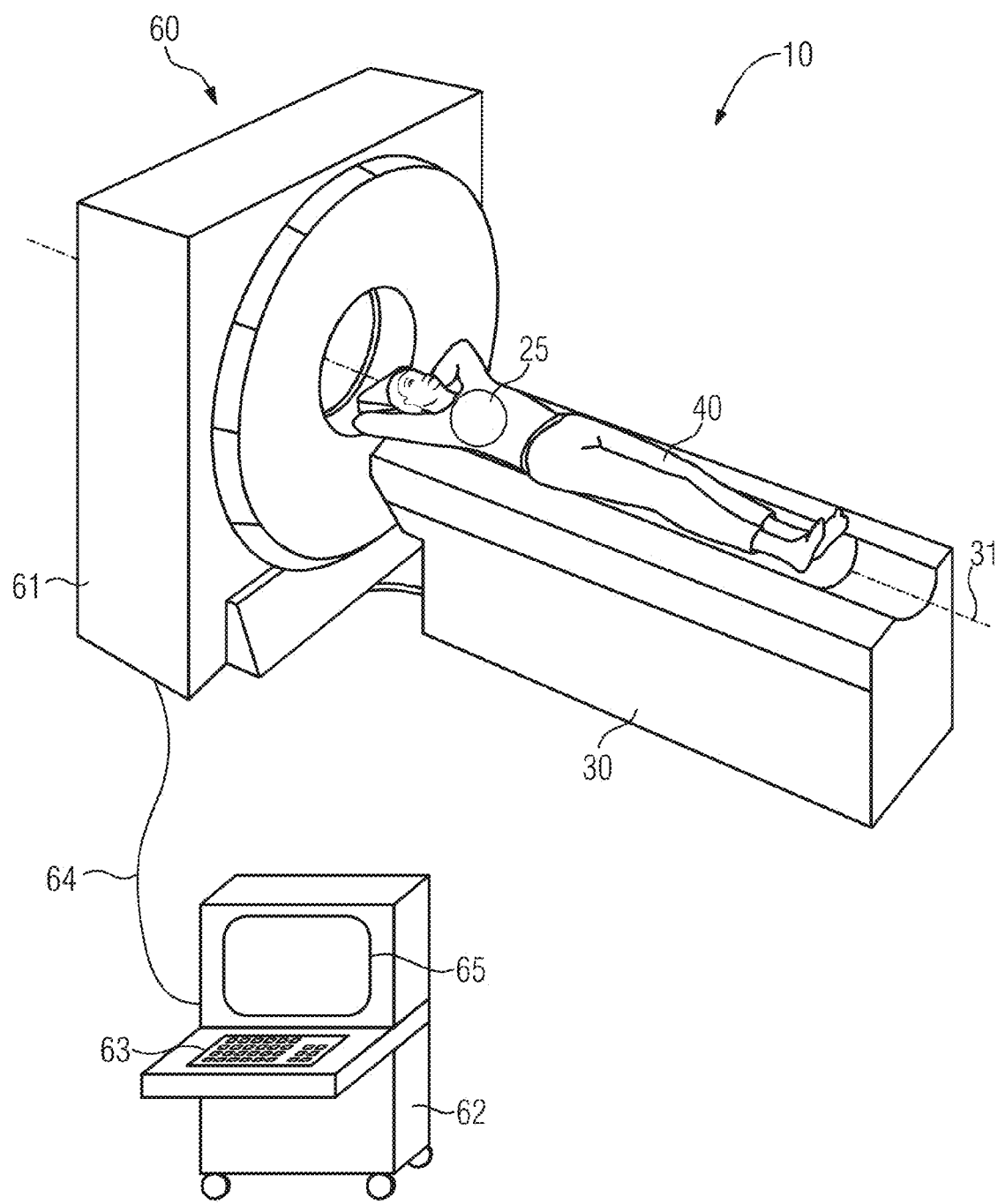
FIG. 4 shows a schematic example of one embodiment of a device for correction of movement artifacts in computed tomography images.

FIG. 4 shows a schematic exemplary embodiment of a device 10 for correction of movement artifacts in a computed tomography image. An image of an examination area 25 (e.g., the heart area of an examination object 40 such as a human patient) is to be obtained with the aid of the computed tomography device 60 with gantry 61. The examination object 40 is supported on a support device 30 (e.g., a patient couch or a patient table). To obtain projection images, the examination object 40 lying on the support device 30 may be moved through the computed tomography device 60 along an axis given by the longitudinal direction of the support device 30. During this process, projections are continuously recorded, which, for example, are made available to a processing and control device 62 (e.g., a processor or a computer) by a connection device 64. In the processor 62, the projections are reconstructed into a computed tomography image or overall image. The processor 62 is thus configured to receive computed tomography projection images that may also cover the examination area 25 of the examination object 40 from the computed tomography device 60, and reconstruct the received computed tomography projection images into a computed tomography image. Through a computer program, for example, that is loaded on and executed on the processor 62, a previously described method for correction of movement artifacts in a computed tomography image may be executed. The computed tomography device 60 has the option of entering an organ program. An operator (e.g., a doctor) with a few entries at an input device 63 (e.g., a computer keyboard of the processor 62) may select a plurality of setting parameters of the computed tomography device 60. For example, after selection of the organ program (e.g., "heart"), the examination area 25 and thus also a probable speed of movement and the periodicity of the movement of the organ "heart" is known to the computed tomography device 62. This information may be incorporated into the method for correction of movement artifacts and may simplify the selection or predetermination of projection images that specify an image volume block. After the method for correction of movement artifacts has been executed in the processor 62, the result (e.g., similar to that shown in FIG. 3) may be displayed on a display 65 (e.g., a computer monitor).

Further embodiments and advantages of the invention are described in summary below. With the aid of the method presented, a plurality of different movement patterns may be corrected. The methods are universally applicable and may be easily adapted to the respective movement pattern. By looking at blocks, the method becomes robust in relation to faults, and time-consuming feature calculations only initially are to be calculated per block and not per projection, so that a more efficient estimation of the movement is produced. Through the described method, a speeding up of the movement correction of computed tomography images may be achieved (e.g., when a block of interest is selected at the beginning of an actual optimization). A region or organ-specific optimization may lead to such optimization methods also being usable in real time or online (e.g., during an intervention).

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for correction of movement artifacts in a computed tomography image that is reconstructed from a plurality of computed tomography projection images, the method comprising:
    determining, by a global optimization method with a processor, an average position of an examination area of an examination object in the reconstructed image volume using all projection images of the plurality of computed tomography projection images; and
    estimating, with the aid of at least one image volume block that is formed from predeterminable projection images, a movement of the examination area of the examination object in the at least one image volume block using an optimization method.

2. The method of claim 1, wherein the average position of the examination area of the examination object determined by the global optimization method is included in the reconstructed image volume in selection of the predeterminable projection images of the at least one image volume block.

3. The method of claim 1, wherein the at least one image volume block comprises at least two image volume blocks that are formed from predeterminable projection images, and at least one projection image belongs to the at least two image volume blocks.

4. The method of claim 1, wherein the predeterminable projection images of each image volume block of the at least one image volume block are specified indirectly or directly by the result of a user entry.

5. The method of claim 4, wherein the user entry is a speed of movement, and the predeterminable projection images of the image volume block are consecutive projection images.

6. The method of claim 1, wherein a measured breathing phase of the examination object, a measured heart phase of the examination object, or the measured breathing phase and the measured heart phase are included in selection of the predeterminable projection images of the at least one image volume block.

7. The method of claim 1, wherein the estimating is executed repeatedly in the at least one image volume block, and
    wherein for each repetition, the at least one image volume block is formed from fewer predeterminable projection images.

8. The method of claim 7, wherein the repetition is executed until a time when the at least one image volume block includes a single projection image.

9. The method of claim 1, wherein the entropy of the reconstructed computed tomography image is included in the global optimization method for determining the average position of the examination area of the examination object in the reconstructed image volume, the entropy of the at least one image volume block is included in the optimization method for estimating the movement of the examination area of the examination object in the at least one image volume block, or a combination thereof.

10. The method of claim 1, wherein the global optimization method, the optimization method, or the global optimization method and the optimization method comprise a gradient descent method.

11. The method of claim 1, wherein the estimating comprises taking at least two image volume blocks into account,
    wherein the at least two image volume blocks overlap, and
    wherein a result of the estimation of the movement of the examination area of the examination object of an image volume block of the at least two image volume blocks is included in the estimation of the movement of the examination area of the examination object of a subsequent image volume block of the at least two image volume blocks.

12. The method of claim 1, wherein the estimations of the movement of the examination area of the examination object of all image volume blocks of the at least one image volume block are included in the correction of movement artifacts of the computed tomography image that is reconstructed from a plurality of computed tomography projection images.

13. The method of claim 1, wherein the predeterminable projection images of an image volume block of the at least one image volume block are determined by the result of a user entry that defines a region, an organ, or the region and the organ.

14. The method of claim 1, wherein a histogram analysis of the projection images is included in selection of the predeterminable projection images of an image volume block of the at least one image volume block.

15. A device for correction of movement artifacts in computed tomography images, the device comprising:
    a computed tomography device; and
    a processor,
    wherein the processor is configured to:
        receive computed tomography projection images from the computed tomograph;
        reconstruct the computed tomography projection images into a computed tomography image; and
        correct movement artifacts in the computed tomography image, the correction comprising:
            determination of an average position of an examination area of an examination object in the reconstructed image volume using all of the computed tomography projection images; and
            estimation, with the aid of at least one image volume block that is formed from predeterminable projection images, a movement of the examination area of the examination object in the at least one image volume block using an optimization method.

* * * * *